United States Patent [19]

Cercek et al.

[11] Patent Number: 4,835,103

[45] Date of Patent: May 30, 1989

[54] DIFFERENTIAL BINDING OF MEMBRANE POTENTIAL SENSITIVE MATERIALS TO LYMPHOCYTES

[76] Inventors: Boris Cercek; Lea Cercek, both of 4318 Camphor Ave., Yorba Linda, Calif. 92686

[21] Appl. No.: 933,982

[22] Filed: Nov. 24, 1986

[51] Int. Cl.$^4$ .................. C12Q 1/02; C12Q 1/04; G01N 33/48

[52] U.S. Cl. .................. 435/29; 424/7.1; 435/34; 436/63

[58] Field of Search ............ 424/7.1, 3; 435/2, 29, 435/34; 436/83

[56] References Cited

U.S. PATENT DOCUMENTS 4,343,782  8/1982  Shapiro .................. 424/3
4,424,201  1/1984  Valinsky et al. .......... 435/35

FOREIGN PATENT DOCUMENTS 0004061  9/1979  European Pat. Off. .

OTHER PUBLICATIONS

Herbert et al., *Dictionary of Immunology*, 3rd Edition, Blackwell Scientific Publications, Oxford, 1985, p. 136.
Peter Jay Sims, Allen S. Waggoner, Chao-Huei Wang and Joseph F. Hoffman, "Studies on the Mechanism by which Cyanine Dyes Measure Membrane Potential in Red Blood Cells and Phosphatidylcholine Vesicles:", *Biochemistry*, 13, p. 3315 (1974).
"The Expanding Use of Potential-Sensitive Dyes", *Nature*, vol. 292, pp. 801–802, Aug. 27, 1981, communication from a correspondent.
"FACS IV, Fluorescence Activated Cell Sorting", published by FACS Systems, a Division of Becton, Dickenson & Co. (Publication date unknown).
L. Cercek, B. Cercek, CIV Franklin, "Biophysical Differentiation Between Lymphocytes from Healthy Donors, Patients with Malignant Diseases and Other Disorders", *Brit J. Cancer*, vol. 29, 345 (1974).
L. Cercek, B. Cercek: "Application of the Phenonmenon of Changes in the Structuredness of Cytoplasmic Matrix (SCM) in the Diagnosis of Malignant Disorders; a Review", *Europ. J. Cancer*, vol. 13, 903–915 (1977).
L. Cercek, B. Cercek: "Involvement of Mitochondria in Changes of Fluorescein Excitation and Emisson Polarization Spectra in Living Cells:", *Biophys. J.*, vol. 28, 403–412 (1979).
L. Cercek and B. Cercek, "Effects of Osmolality and Density of Gradients on the Isolation of SCM-Responding Lymphocytes", *Br. J. Cancer*, vol. 38, p. 163 (1978).
L. Cercek and B. Cercek, "Apparent Tumor Specificity with the SCM Test, a short Communication", *Brit J. Cancer*, vol. 31, p. 252 (1975).

Primary Examiner—Robert J. Warden
Assistant Examiner—David A. Saunders
Attorney, Agent, or Firm—Sheldon & Mak

[57] ABSTRACT

The method of the present invention comprises contacting a suspension of viable lymphocytes with a solution containing a membrane potential sensitive fluorescent dye. The contact between the lymphocyte suspension and the MPS dye is maintained for sufficient time to permit labelling of the lymphocytes by the MPS dye material. The labelled lymphocytes are passed individually through a focused source of excitation energy causing any MPS dye material to fluoresce. The fluorescent emission from each cell is recorded as a pulse and the number of pulses of each intensity are recorded. The distribution of the number of pulses versus the intensity is prepared distribution is bimodal. A first peak includes pulses of low fluorescence intensity and a second peak comprises pulses of high fluorescence intensity. A ratio of the total counts of low fluorescence intensity to the total counts of high fluorescence intensity produces a factor which distinguishes lymphocytes derived from bodies afflicted with malignancy from bodies which are not afflicted with malignancy.

13 Claims, 1 Drawing Sheet

DIFFERENTIAL BINDING OF MEMBRANE POTENTIAL SENSITIVE MATERIALS TO LYMPHOCYTES

FIELD OF THE INVENTION

The present invention relates to the differential binding of membrane potential sensitive materials by lymphocytes and more particularly to a method for the detection of a malignancy in a body utilizing differential binding of potential sensitive materials by lymphocytes.

BACKGROUND OF THE INVENTION

In recent years there has been increased interest in the use of biological probes, such as membrane potential sensitive dye materials, to determine changes in the membrane potential of living cells and/or other cellular structures in electrophysiological and biophysical studies of living cells. For example, such materials have been used to study membrane potential in squid giant axon cells, Cohen LPB et al. *J. Membrane Biol.* 19,1 (1974), in red blood cells, Hoffmann, J. R. and Laris, P. C., *Physiol. Lond.* 239, 519 (1974), and for frog heart muscular tissue, Morad, M. and Selema, G., *J. Physiol.* Lond. 292 267 (1972).

Along this same vein the study of blood cell physiology is leading to methods for detection of disease states in human and animal bodies. For example, we have developed a method for the early detection of cancer and other antigen producing disease and body conditions employing intracellular fluroescein fluorescence polarization measurements in living cells to study changes in the structuredness of cytoplasmic matrix (SCM). SCM includes various cell structures such as, for example, mitochondria, cell membranes, cell sap, lysosomes, ribosomes, nuclei and the like. Our method, which is referred to in literature as the "SCM-Test", and the technique employed is summarized in a publication by L. Cercek, B. Cercek, "Application of the Phenomenon of Changes in the Structuredness of Cytoplasmic Matrix (SCM) in the Diagnosis of Malignant Disorders: A Review", *Europ. J. Cancer*, Vol. 13, 903–915 (1977). Using our techniques, early diagnosis of cancer and other types of diseases and body conditions is readily accomplished by measuring the differential responses of a density specific subpopulation of peripheral blood lymphocytes to, for example, mitogen phytohaemagglutinin and to cancer associated antigens. Changes in intracellular fluorescein fluorescence polarization are used to indicate the differential responses of the lymphocytes.

The above described method, however, requires very highly skilled personnel and extremely careful techniques in order to separate and isolate the subpopulation of SCM-responding lymphocytes from the blood sample and to carry out the fluorescence measurements. In addition the SCM-Test technique demands microanalytical precision in the intracellular fluorescence polarization measurements, high instrument sensitivity and stability. Poor technique and unskilled handling of lymphocytes sensitive to perturbations of the metabolic state can result in unreproduceable, and totally erroneous test results.

Accordingly, it would be highly desirable to provide a screening technique for the detection of cancer which is simpler and less expensive to run and which can be reliably carried out with a lower degree of technical proficiency using readily available equipment thereby rendering the methodology of such a screening technique practical for routine use in clinical laboratories and even in the doctor's office.

SUMMARY OF THE INVENTION

The present invention provides a method for screening blood samples for the presence of a malignancy in the donor body utilizing commercially available instrumentation to detect and record test results. The methodology of the invention is based upon differential uptake of a membrane potential sensitive material by a certain subpopulation of lymphocytes, which uptake differs depending upon whether or not the donor body is afflicted with a malignancy. Although the methodology defined herein still requires a degree of proficiency in the isolation of the correct density specific subpopulation of lymphocytes, it is less demanding and more easily carried out by one skilled in the art. The method of the invention employs flowcytometry techniques and instrumentation which are well understood and readily available and the handling of the lymphocytes is less critical than in the previously described SCM-Test. The present method is particularly suited for use as a routine cancer screening procedure which can be used in conjunction with the aforementioned SCM-Test, which is capable of very early and specific diagnosis of a malignancy.

The method of the present invention comprises contacting a suspension of viable lymphocytes with a solution containing a membrane potential sensitive fluorescent material. Such materials, which are conventionally referred to as membrane potential sensitive fluorescent dyes will be referred to hereinafter as "MPS dyes". The contact between the lymphocyte suspension and the MPS dye is maintained for sufficient time to permit labelling of the lymphocytes with the MPS dye material.

Following the labelling operation as described above the now labelled lymphocytes are passed as single cells through a focused source of excitation energy to cause any MPS dye material with which the lymphocytes have been labelled, to fluoresce. The fluorescent emission from each cell is recorded as a pulse and the number of pulses of each intensity are stored. A plot of the distribution of the number of pulses versus pulse intensity of the fluorescence emissions from the labelled lymphocytes is a bi-model curve, i.e. the curve comprises two peaks. The first peak of the curve includes pulses of low fluorescence intensity and the second peak comprises pulses of high fluorescence intensity. A ratio of the total number of low fluorescence pulses to the high fluorescence pulses for each sample tested produces a factor which differentiates lymphocytes derived from donors afflicted with cancer from those which are not afflicated with cancer. This factor, which is referred to herein as the alpha factor, has been found to be less than 2.6 for lymphocyte suspensions derived from donors afflicted with a malignancy. On the other hand alpha factors greater than 2.6 are associated with lymphocyte samples derived from donors which are not afflicted with a malignancy. On this basis the method of the present invention provides a screening test for the presence of cancer which is relatively simple, economical and which requires only an ordinary degree of technical skill to carry out.

BRIEF DESCRIPTION OF THE DRAWINGS

The invention will be more fully understood from the detailed description of the invention taken in conjunction with the drawings in which.

DETAILED DESCRIPTION OF THE INVENTION

Figure 1:
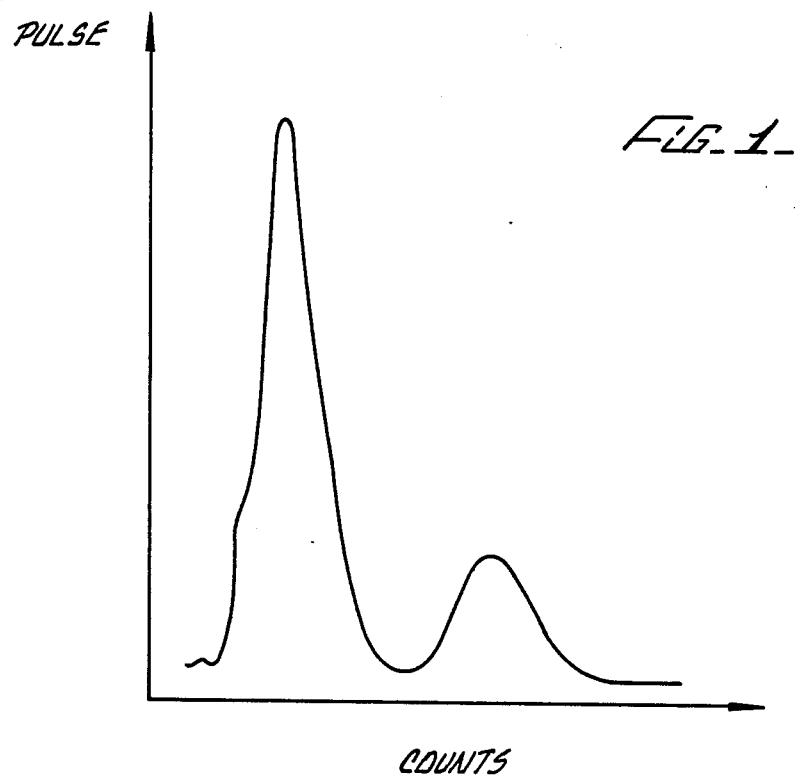
FIG. 1 is a representative plot of the pulse distributions of fluorescent emissions from a typical lymphocyte sample derived from a donor not afflicted with malignancy.

The cells utilized in the method of the present invention are lymphocytes separated from a sample of blood taken from a body being tested. Although it is not presently fully understood, it is believed that lymphocytes, which are the T-cell type, are involved in the recognition of malignancy associated antigens. Certain lymphyocytes, referred to as SCM-responding lymphocytes, derived from donors afflicted with cancer have been primed in vivo to recognize malignancy associated antigens, such as are formed by tumor cells, and accordingly have been found to have a different response to MPS dyes than do lymphocytes derived from a donor not afflicated with a malignancy.

The lymphocytes useful in the present invention are most conveniently separated from the blood sample by centrifugation of the blood sample on a density gradient solution, such as a mixture of Ficoll 400 (Pharmacia A B) and Triosil 440 (Nyegaard & Co.) solutions. Blood cells having a density less than that of the gradient solution float on top of the gradient solution and can be separated from cells having densities greater than that of the gradient solution. Such a method for separation of blood components is well understood in the art, such as for example, the technique published by R. Harris, E. Ukaejiofo, *Lancet*, Vol. 2, 327 (1969). By modification of the gradient solution to the separation density of 1.08 g/cm$^3$ at 25° C. and osmolality of 0.320 Osm/kg, the SCM-responding luymphocytes will float on the gradient solution after centrifugation of a blood sample and are readily separated by aspirating the cell layer directly above the plasma gradient solution interface, as described by L. Cercek, B. Cercek *Br. J.Cancer*, Vol. 38, 163 (1978).

After separation from gradient solution the cells are washed, preferably twice, with preservative free sodium chloride solution for injections and then, preferably twice, with complete Dulbecco's phosphate buffered saline (PBS). Following washing, the cells are suspended in PBS for use in the test method of the present invention. The concentration of cells in the suspension is not critical, although an adequate number of cells must be present in the suspension to develop the fluorescence intensity distribution curve as will be explained in more detail hereinafter. Good results have been achieved in accordance with the preferred embodiment of the invention utilizing lymphocyte suspension concentrations on the order of 10$^6$ cells per ml.

MPS dyes are materials which contain a fluorochrome and which are capable of binding on or penetrating the cell membrane. The exact mechanism by which MPS dyes work is not clear although several models have been proposed, Sims, et al., *Biochemistry* 13, 3315 (1974).

MPS dye materials suitable for use in the present invention are selected from the group consisting of the cyanine dyes, the merocyanine dyes and the oxonol dyes. Among the merocyanine dyes are merocyanine oxazolone and merocyanine rhodanine. The most widely investigated and the preferred group of dyes are the cyanine dyes which have been prepared and studied by Sims, et al., *Biochemistry* 13, 3315 (1974). In this publication some 29 cyanine dyes were studied with respect to the effect on the dye of the changes in cell membrane potentials. A commercially available cyanine dye with which good results have been obtained in the present invention is 3,3'- dihexyloxacarbocyanine. In accordance with the convention set forth in the Sims, et al, publication, this dye will be identified by its shorthand notation, diO—C$_6$—(3). . The MPS dye material is used in the present invention as a dilute solution of the dye in PBS. In the solution, the concentration of the MPS dye ranges from between about $2 \times 10^{-6}$ to about $5 \times 10^{-6}$ and preferably is about $3 \times 10^{-6}$ grams per ml. Since many of the MPS dye materials are only sparingly soluble in the phosphate buffered saline, it is preferred to first form a more concentrated solution of the MPS dye material in ethyl alcohol followed by dilution of the concentrated alcohol solution to the desired concentration with PBS. After the lymphocyte suspension is prepared as described above, the lymphocytes are then labelled with the MPS dye material. The labelling operation is most conveniently carried out by admixture of equal parts of the lymphocyte solution with the dilute solution of the MPS material and, with continued gentle stirring, the lymphocyte suspension dye soltution mixture is maintained for a suitable period to permit the labelling of the lymphocytes by the MPS material. Normally a contact time of about 10 minutes is sufficient to effect labelling of the lymphocytes although contact can be maintained for as long as 1 hour without damaging the lymphocytes. We have found that best results are achieved by maintaining the temperature of the lymphocyte suspension/dye solution mixture at room temperature (20° C.–23° C.) during the labelling operation.

Following the contact between the cell suspension and the MPS dye solution, the cells are passed through a focused source of fluorescence excitation energy which causes the MPS dye material to fluoresce. This is accomplished in a fluorescence activated cell sorter wherein the labelled lymphocyte suspension is injected into a stream of a sheath fluid which is flowing at sufficient velocity through a small diameter tube to establish a laminar coaxial flow of the lymphocytes within the sheath fluid. In this manner the individual lymphocytes are separated to form a stream of individual cells within the sheath fluid. A laser beam comprises the focused source of excitation energy and the beam is caused to impinge on the flowing stream of fluid substantially normal to the direction of the flow. In this fashion, each individual lymphocyte is interrogated by the laser beam as it flows therepast. Suitable photoelectric detection devices are positioned downstream of the point at which the laser beam interrogates the lymphocytes and the fluorescence intensity of each of the lymphocytes is detected as a pulse as it passes the photoelectric detecting device. The pulse intensity is forwarded to a pulse counter where the count of that pulse is stored in a channel segregated for the particular intensity of the pulse. In this fashion the number of pulses at each pulse intensity is stored for use in developing the distribution curve.

Figure 2:
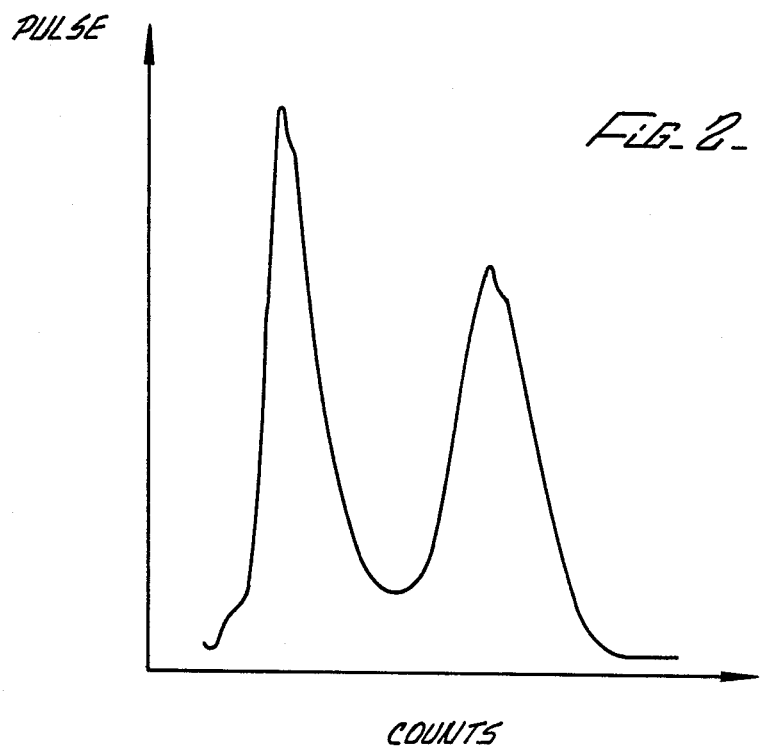
FIG. 2 is a representative plot of the pulse distribution of fluorescent emissions of lymphocytes derived from a donor afflicated with a malignancy.

As illustrated in FIGS. 1 and 2, when plotted as pulse height (corresponding to fluorescence intensity) as the abscissa and the number of counts at that pulse height as the ordinate, the data from each sample of lymphocytes forms a bi-model curve. The first peak (left peak) on the distribution curve represents low intensity lymphocytes while the second peak (right hand peak) on the distribution curve represents high intensity lymphocytes. We have unexpectedly found that the ratio of the number of cells in the left hand peak to the number of cells in the right hand peak (alpha ratio) is directly related to the presence or absence of a malignancy in the body of the donor from which the lymphocytes were isolated. For example, the curve illustrated in FIG. 1 represents a distribution curve of lymphocytes isolated from a donor not afflicted with a malignancy. It will be seen that the left peak representing low intensity pulses is substantially larger than the right peak which represents high intensity pulses. In the case of the distribution curves of the fluorescent emissions labelled cells derived from donors not afflicated with a cancer, such as represented by FIG. 1, the ratio of the left peak to the right peak is greater than 2.6.

FIG. 2, on the other hand, represents a typical distribution curve for lymphocytes isolated from a donor who was definitely diagnosed as having a malignancy. In this case the difference between number of high intensity pulses and low intensity pulses is not as great as in FIG. 1 and the ratio of the left peak to the right peak is less than 2.6.

The reaosn for the difference in ratio of left peak to right peak between donors having malignancies and those who do not is not completely understood. However, it is hypothesized that the membrane potential of a large fraction of lymphocytes from donors with neoplastic diseases are somewhat more electronegative thus resulting in a greater binding of MPS dye material to the cell and/or penetration of the cell by the dye which increases cell labelling. Also, the increased negativity of the membrane potential of that fraction of lymphocytes may cause the MPS dye to fluoresce more intensely. In any case this would produce a greater number of counts of high intensity pulses as compared to low intensity pulses thus bringing the alpha ratio down below 2.6. In contrast, lymphocytes from donors not afflicated with neoplastic diseases are believed to be less electronegative thus resulting in lower binding of MPS dye to the lymphocytes and/or, for the reasons stated above, lower intensity fluorescence emissions by the MPS dye material. Accordingly, this should produce a larger number of counts for lymphocytes of low intensity as compared to those of high intensity thus bringing the alpha ratio above 2.6.

The selection of excitation and emission wavelengths is primarily dependent on the choice of MPS dye material utilized in the method. With cyanine dyes, the preferred MPS dye materials, we have found that highly satisfactory results are achieved when the laser beam wavelength is 488 nm and fluorescence emissions at wavelengths above 520 nm are recorded. As has been pointed out by Sims, et al., *Biochemistry*, 13, 3315 (1974), the fluorescence emissions for the cyanine dyes range from approximately 496 nm up to 792 nm. With the equipment available, wew have obtained good results measuring fluorescence emissions above 520 nm. Example Lymphocytes were separated from samples of 20 ml samples of peripheral blood by layering an aliquot of the blood sample from which the phagocytic cells had been removed on a Ficoll-Triosil density gradient solution having a density of 1.081 g/cm$^3$ at 25° C. and an osmolality of 0.320 osm/kg. The blood sample and density gradient solution were centrifuged at 550 $G_{av}$ at a temperature of 25° C. The narrow layer floating immediately above the interface of the plasma and the gradient solution material was aspirated with a Pasteur pipette avoiding as much as possible any of the heavier density gradient material and the lighter plasma materials floating above the separated layer of cells. The presence of some of these materials in the removed cells sample is, however, not critical in the present technique. This separation technique follows generally the technique set forth by L. Cercek, B. Cercek, "Application of the Phenomena of Changes in the Structuredness of Cytoplasmic Matrix (SCM) in the Diagnosis of Malignant Disorders: a Review", *Europ. J. Cancer*, Vol. 13, 903–915 (1977) and by the same authors in a publication entitled "Effects of Osmolality and Density of Gradients on the Isolation of SCM-Responding Lymphocytes", *Br. J. Cancer*, Vol. 38, 163–165 (1978). However, as mentioned above, the separation technique is not as critical as set forth in the aforementioned publications and the method of the present invention is not limited to the very specific sub-population of lymphocytes required for the technique set forth in the publications. Accordingly the technique employed in the present method for the separation of the lymphocytes from the remaining blood components and the subsequent handling of the separated cells is far less critical than required by the above referenced publications.

Blood samples were obtained from 15 age and sex matched healthy donors, i.e. donors who were not diagnosed as having a malignancy, and 15 donors who were positively diagnosed as having cancer. For the purposes of this example the specific type of cancer is not critical. Blood samples were also obtained from 6 donors who were diagnosed as having non-malignant inflammatory diseases, such as arthritis and other inflammatory conditions. The lymphocyte fractions isolated from each of the blood samples, according to the procedure described above, were washed with 6 to 7 ml of a 0.9% solution of NaCl without preservatives followed by washing in PBS. Between washes each cell suspension was centrifuged at 500 $G_{av}$ and the supernatant liquid was decanted. After washing, the cell suspension from each sample was recombined with PBS and the volume adjusted to form a suspension of about $2 \times 10^6$ cells per ml.

A labelling solution of diO—$C_6$—(3) was prepared by first dissolving 28.6 mg of the dye in 10 ml of absolute "analar grade" ethanol. The solution was adjusted to its final concentration by injecting 0.1 ml of the stock solution into 100 ml of PBS.

Labelling was effected by combining equal volumes of the labelling solution and the lymphocyte suspension and maintaining the mixture with light stirring for at least 10 minutes. At the completion of the labelling procedure fluorescent distributions were recorded on a Becton-Dickinson flow cytometer, model FACS IV. The MPS dye labelled cells were excited with a 488 nm argon ion laser line and fluorescence emissions above 520 nm were recorded using the standard FACS IV optical filters. The FACS IV cytometer was provided with a computer, which served as a pulse analyzer for recording and sorting the pulses obtained from the sample. A stream of individual cells was produced, as described above, by introducing the suspension of cells in the labelling solution into the center of a flowing stream of compatible sheath fluid, thus establishing a laminar coaxial flow within the nozzle-transducer assembly of the FACS IV instrument. In this manner the sample fluid and the cells contained therein were constrained to the central portion of the liquid flowstream, thus preventing the cells from touching the instrument nozzle assembly and providing a flow of individual cells past the laser beam. The fluorescence emissions from cells flowing past the laser beam were detected by a photomultiplier and the intensity translated into an electrical pulse which was stored by the pulse analyzer. The pulse analyzer sort, when plotted as frequency of pulses vs pulse height produced curves such as the typical curves illustrated in FIGS. 1 and 2. The total counts of the left NL and right NR peaks and the resulting alpha ratio for donors diagnosed as being free of cancer are set forth in Table 1 below. The results for donors diagnosed as having cancer and donors diagnosed as having inflammatory diseases such as arthritis, are set forth in Table II and Table III respectively.

TABLE I

| Run No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Donor* Type | H | H | H | H | H | H | H | H | H | H | H | H | H | H | H |
| NL/1000 | 70.4 | 48.2 | 156.8 | 89.5 | 56.8 | 85.0 | 31.9 | 34.7 | 86.7 | 65.5 | 82.3 | 62.1 | 49.0 | 60.4 | 48.3 |
| NR/1000 | 11.3 | 9.0 | 30.3 | 20.8 | 14.0 | 21.3 | 8.5 | 9.5 | 24.4 | 20.3 | 24.9 | 19.3 | 15.1 | 22.0 | 17.9 |
| Alpha Factor | 6.2 | 5.35 | 5.15 | 4.3 | 4.0 | 4.0 | 3.75 | 3.65 | 3.5 | 3.3 | 3.3 | 3.25 | 3.25 | 2.75 | 2.7 |

*Donor Type: H (healthy, no cancer), C (diagnosed as having cancer), I (diagnosed as having inflamatory disease)

TABLE II

| Run No. | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| Donor* Type | C | C | C | C | C | C | C | C | C | C | C | C | C | C | C |
| NL/1000 | 52.8 | 53.2 | 44.5 | 21.6 | 13.4 | 28.1 | 49.2 | 50.3 | 67.5 | 22.1 | 58.6 | 18.3 | 48.3 | 53.3 | 60.4 |
| NR/1000 | 20.7 | 24.2 | 20.2 | 10.7 | 6.9 | 15.4 | 29.0 | 30.5 | 40.9 | 14.7 | 39.3 | 15.2 | 42.1 | 53.4 | 35.5 |
| Alpha Factor | 2.55 | 2.2 | 2.2 | 2.0 | 1.95 | 1.9 | 1.7 | 1.65 | 1.65 | 1.5 | 1.49 | 1.2 | 1.15 | 1.0 | 1.7 |

*Donor Type: H (healthy, no cancer), C (diagnosed as having cancer), I (diagnosed as having inflamatory disease)

TABLE III

| Run No. | 31 | 32 | 33 | 34 | 35 | 36 |
|---|---|---|---|---|---|---|
| Donor* Type | I | I | I | I | I | I |
| $N_L$/1000 | 24.6 | 160.2 | 142.5 | 111.5 | 54.7 | 309.6 |
| $N_R$/1000 | 5.5 | 14.6 | 14.2 | 23.5 | 9.5 | 33.5 |
| Alpha Factor | 4.5 | 11.0 | 10.0 | 4.75 | 5.76 | 9.24 |

*Donor Type: H (healthy, no cancer), C (diagnosed as having cancer), I (diagnosed as having inflammatory disease)

From the results of the example it it seen that in no case do the alpha factors for lymphocytes from donors afflicated with a malignancy exceed 2.6. By the same token the alpha factors for lymphocytes from donors who do not have malignancies do not fall below 2.6. This is true even when the donors is afflicteed with other inflammatory disease conditions such as arthritis.

From the foregoing it will be seen that the method of the present invention provides a simple test for screening the blood samples of donors for the presence of a malignancy in the donor's body. The test requires a relatively small blood sample and can be carried out by persons of ordinary skill in the art. While the invention has been described and illustrated herein with reference to certain embodiments thereof, it is to be unserstood that it may be otherwise embodied within the scope of the appended claims.

We claim:

1. A method for the determination of a malignancy in a human or animal body comprising the steps of:
    (a) obtaining a fraction consisting essentially of SMM-responding lymphocytes derived from a sample of blood from said body;
    (b) labelling said lymphocytes by contacting a suspension of said lymphocytes with a fluorescent cell membrane potential sensitive material such that said membrane potential sensitive material is bound to said lymphocytes;
    (c) causing said lymphocytes to pass individually through a focused source of fluorescence excitation energy causing said membrane potentail sensitive material to fluoresce;
    (d) measuring the intensity of the fluorescence emission from each of said lymphocytes; and
    (e) forming a bimodal distribution curve based on the measured intensity of the fluorescence emission of said lymphocytes and determining a ratio therefrom of the number of lymphocytes of lower fluorescence intensities to the number of lymphocytes of higher fluorescence intensities, said ratio then being compared to a predetermined cutoff value, such that when said ratio is lower than the predetermined cutoff value it is indicative of the presence of a malignancy in said body.

2. The method of claim 1 wherein said membrane potential sensitive material is a fluorescent dye selected from the group consisting of the cyanine dyes, merocyanine dyes and the oxonol dyes.

3. The method of claim 2 wherein said membrane sensitive material is a cyanine dye selected from the group consisting of carbocyanine, dicarbocyanine and tricarbocyanine dyes.

4. The method of claim 3 wherein said membrane potential sensitive material is 3,3'-dihexyloxacarbocyanine.

5. The method of claim 1 wherein said suspension of lymphocytes is in phosphate buffered saline solution and comprises about $2 \times 10^6$ cells per milliliter of phosphate buffered saline solution.

6. The method of claim 1 wherein said suspension of lymphocytes is mixed with equal parts by volume of a solution comprising about $2.86 \times 10^{-6}$ g/ml of said membrane potential sensitive material in phosphate buffered saline solution and maintaining said mixture for sufficient time to effect binding of a sufficient quantity of said material to said lymphocytes to cause said lymphocytes to emit fluorescence when passed individually through said focused source of fluorescence excitation energy.

7. The method of claim 6 wherein said mixture is maintained for at least about 10 minutes.

8. The method of claim 1 wherein said source of excitation energy is a laser beam.

9. The method of claim 8 wherein said laser beam has a wavelength of 488 nm.

10. The method of claim 1 wherein said labeled lymphocytes are injected into a flowing stream of a compatible sheath fluid and a laminar, coaxial flow of said lymphocytes and said sheath fluid is established whereby said lymphocytes are constrained as individual cells in the center portion of said flowing stream prior to passing through said source of excitation energy.

11. The method of claim 1 wherein the intensity of fluorescence emissions from each of said lymphocytes is converted to an electrical pulse, the height of which is directly related to the intensity of the emission, and plotted on a distribution curve with pulse height as the abscissa and pulse counts as the ordinate, said distribution curve being bimodal with one peak representing lower intensity emissions and the other peak representing higher intensity emissions.

12. The method of claim 11 wherein the number of pulses in the peak representing higher intensity emissions is divided into the number of pulses in the peak representing lower intensity emission to obtain an alpha factor that is characteristic for lymphocytes derived from a body afflicted with a malignancy and for lymphocytes derived from a malignancy free body.

13. The method of claim 12 wherein lymphocytes derived from a body afflicted with a malignancy have an alpha factor of less than 2.6, and lymphocytes derived from a malignancy-free body have an alpha factor of greater than 2.6.

* * * * *